(12) United States Patent
DeLuca et al.

(10) Patent No.: US 7,208,484 B2
(45) Date of Patent: *Apr. 24, 2007

(54) METHOD OF SYNTHESIZING 1ALPHA-HYDROXY-2-METHYLENE-19-NOR-HOMOPREGNACALCIFEROL

(75) Inventors: Hector F. DeLuca, Deerfield, WI (US); Sumithra Gowlugari, Fremont, CA (US); Rafal R. Sicinski, Warsaw (PL)

(73) Assignee: Wisconsin Alumni Research Foundation, Madison, WI (US)

( * ) Notice: Subject to any disclaimer, the term of this patent is extended or adjusted under 35 U.S.C. 154(b) by 212 days.

This patent is subject to a terminal disclaimer.

(21) Appl. No.: 10/847,040

(22) Filed: May 17, 2004

(65) Prior Publication Data

US 2004/0220418 A1   Nov. 4, 2004

Related U.S. Application Data

(63) Continuation of application No. 10/397,135, filed on Mar. 26, 2003, now Pat. No. 6,774,251.

(60) Provisional application No. 60/369,159, filed on Mar. 29, 2002.

(51) Int. Cl.
*A61K 31/593* (2006.01)
*C07C 401/00* (2006.01)

(52) U.S. Cl. .................................. 514/167; 552/653
(58) Field of Classification Search ................ 514/167; 552/653
See application file for complete search history.

(56) References Cited

U.S. PATENT DOCUMENTS

| | | | |
|---|---|---|---|
| 4,666,634 A | 5/1987 | Miyamoto et al. | |
| 4,800,198 A | 1/1989 | DeLuca et al. | |
| 5,089,641 A | 2/1992 | DeLuca et al. | |
| 5,536,713 A | 7/1996 | DeLuca et al. | |
| 5,578,587 A | 11/1996 | DeLuca et al. | |
| 5,587,497 A | 12/1996 | DeLuca et al. | |
| 5,843,928 A | 12/1998 | DeLuca et al. | |
| 5,877,168 A | 3/1999 | Miyamoto et al. | |
| 5,936,105 A | 8/1999 | Paaren | |
| 5,936,133 A | 8/1999 | Deluca et al. | |
| 5,945,410 A | 8/1999 | DeLuca et al. | |
| 6,277,837 B1 | 8/2001 | DeLuca et al. | |
| 6,306,844 B1 | 10/2001 | DeLuca et al. | |
| 6,566,352 B1 * | 5/2003 | DeLuca et al. | 514/167 |
| 6,579,861 B2 * | 6/2003 | DeLuca et al. | 514/167 |
| 6,627,622 B2 * | 9/2003 | DeLuca et al. | 514/167 |
| 6,774,251 B2 * | 8/2004 | DeLuca et al. | 552/653 |
| 6,992,074 B2 * | 1/2006 | DeLuca et al. | 514/167 |

FOREIGN PATENT DOCUMENTS

WO   WO 02/20021   3/2002

OTHER PUBLICATIONS

Brown et al, "New Active Analogues of Vitamin D with Low Calcemic Activity" Kidney International, vol. 38, Suppl. 29 (1990) pp. S-22-S-27.

Hareau et al, "Asymmetric Synthesis of $1_\alpha,25$-Dihydroxyvitamin $D_3$ A-Ring Precursor Starting with 5-Tert-Butyldimethylsiloxy-2-Cyclohexenone" Tetrahedron Letters, 41 (2000) pp. 2385-2388.

Sicinski et al, "New $1_\alpha,25$-Dihydroxy-19-Norvitamin $D_3$ Compounds of High Biological Activity: Synthesis and Biological Evaluation of 2-Hydroxymethyl, 2-Methyl, and 2-Methylene Analogues" J. Med. Chem., 41 (1998) pp. 4662-4674.

* cited by examiner

*Primary Examiner*—Sabiha N. Qazi
(74) *Attorney, Agent, or Firm*—Andrus, Sceales, Starke & Sawall, LLP

(57) ABSTRACT

A method of making 1α-hydroxy-2-methylene-19-nor-homopregnacalciferol. The method includes the steps of condensing a bicyclic ketone with an allylic phosphine oxide to produce a protected 19-nor-pregnacalciferol analog, thereafter cleaving the protecting group to form 22-alcohol, converting the alcohol to an ester, reducing the ester to 17β-isopropyl-19-nor-vitamin D analog, and finally deprotecting the 17β-isopropyl derivative to form the desired compound.

12 Claims, No Drawings

METHOD OF SYNTHESIZING 1ALPHA-HYDROXY-2-METHYLENE-19-NOR-HOMOPREGNACALCIFEROL

CROSS-REFERENCE TO RELATED APPLICATIONS

This application is a continuation of application Ser. No. 10/397,135 filed Mar. 26, 2003, now U.S. Pat. No. 6,774,251 which is based on and claims priority from provisional patent Application No. 60/369,159 filed on Mar. 29, 2002.

BACKGROUND OF THE INVENTION

The natural hormone, 1α,25-dihydroxyvitamin $D_3$ and its analog in the ergosterol series, i.e. 1α,25-dihydroxyvitamin $D_2$ are known to be highly potent regulators of calcium homeostasis in animals and humans, and more recently their activity in cellular differentiation has been established, Ostrem et al., Proc. Natl. Acad. Sci. USA, 84, 2610 (1987). Many structural analogs of these metabolites have been prepared and tested, including 1α-hydroxyvitamin $D_3$, 1α-hydroxyvitamin $D_2$, various side chain homologated vitamins and fluorinated analogs. Some of these compounds exhibit an interesting separation of activities in cell differentiation and calcium regulation. This difference in activity may be useful in the treatment of a variety of diseases such as renal osteodystrophy, vitamin D-resistant rickets, osteoporosis, psoriasis, and certain malignancies.

Recently, a new class of vitamin D analogs has been discovered, i.e. the so called 19-nor-vitamin D compounds, which are characterized by the replacement of the A-ring exocyclic methylene group (carbon 19), typical of the vitamin D system, by two hydrogen atoms. Biological testing of such 19-nor-analogs (e.g., 1α,25-dihydroxy-19-nor-vitamin $D_3$) revealed a selective activity profile with high potency in inducing cellular differentiation, and very low calcium mobilizing activity. Thus, these compounds are potentially useful as therapeutic agents for the treatment of malignancies, or the treatment of various skin disorders. Two different methods of synthesis of such 19-nor-vitamin D analogs have been described [Perlman et al., Tetrahedron Lett. 31, 1823 (1990); Perlman et al., Tetrahedron Lett. 32, 7663 (1991), and DeLuca et al., U.S. Pat. No. 5,086,191)].

In U.S. Pat. No. 4,666,634, 2β-hydroxy and alkoxy (e.g., ED-71) analogs of 1α,25-dihydroxyvitamin $D_3$ have been described and examined by Chugai group as potential drugs for osteoporosis and as antitumor agents. See also Okano et al., Biochem. Biophys. Res. Commun. 163, 1444 (1989). Other 2-substituted (with hydroxyalkyl, e.g., ED-120, and fluoroalkyl groups) A-ring analogs of 1α,25-dihydroxyvitamin $D_3$ have also been prepared and tested (Miyamoto et al., Chem. Pharm. Bull. 41, 1111 (1993); Nishii et al., Osteoporosis Int. Suppl. 1, 190 (1993); Posner et al., J. Org. Chem. 59, 7855 (1994), and J. Org. Chem. 60, 4617 (1995). Recently, similar analogs of 1α,25-dihydroxy-19-norvitamin $D_3$ have also been synthesized, i.e., compounds substituted at 2-position with hydroxy or alkoxy groups (DeLuca et al., U.S. Pat. No. 5,536,713), which exhibit interesting and selective activity profiles. All these studies indicate that binding sites in vitamin D receptors can accommodate different substituents at C-2 in the synthesized vitamin D analogs.

Recently analogs which are characterized by the transposition of the ring A exocyclic methylene group, present in the normal vitamin D skeleton, from carbon 10 (C-10) to carbon 2 (C-2), i.e., 2-methylene-19-nor-vitamin D compounds, were synthesized and tested. Molecular mechanics studies indicate that such molecular modification does not change substantially the conformation of the cyclohexanediol ring A. However, introduction of the 2-methylene group into 19-nor-vitamin. D carbon skeleton changes the character of its (1α- and 3β-) A-ring hydroxyls. They are both now in the allylic positions, similarly, as 1α-hydroxy group (crucial for biological activity) in the molecule of the natural hormone, 1α,25-$(OH)_2D_3$. These analogs have exhibited similar rate of binding to the receptor as 1α,25-dihydroxyvitamin $D_3$ and were also characterized by high cell differentiation activity. These compounds were characterized by little, if any, intestinal calcium transport activity, as compared to that of 1α,25-dihydroxyvitamin $D_3$, while exhibiting relatively high activity, as compared to that of 1α,25-dihydroxyvitamin $D_3$ in their ability to mobilize calcium from bone.

More than ten years ago an interesting 1α-hydroxyvitamin D analog was synthesized, namely, 1α-hydroxy-20-methyl-pregnacalciferol (also sometimes referred to as 1α-hydroxy-homopregnacalciferol) which was essentially devoid of calcemic activity, showed some HL-60 cell differentiation ability but unexpectedly exhibited comparable binding to the receptor as 1α,25-dihydroxyvitamin $D_3$ [Lau, W. F. (1986) Ph.D. Thesis, University of Wisconsin-Madison]. In a continuing effort to explore the 19-nor class of pharmacologically important vitamin D compounds, a 1α-hydroxy-19-nor-vitamin D analog, which is characterized by the presence of methylene substituent at the carbon 2 (C-2) and 17β-isopropyl side chain has now been synthesized and tested.

SUMMARY OF THE INVENTION

The present invention is directed toward a method of making 1α-hydroxy-2-methylene-19-nor-homopregnacalcifeol having the structure

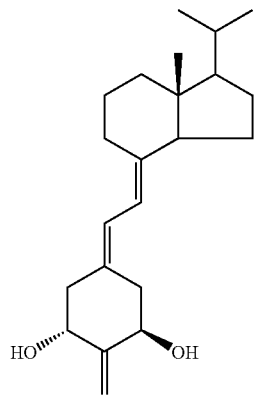

comprising the steps of:
 condensing a bicyclic ketone having the structure

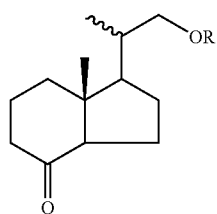

with an allylic phosphine oxide having the structure

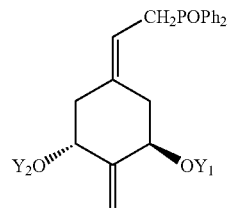

where $Y_1$, $Y_2$ and R, which may be the same or different, are each a hydroxy-protecting group, to produce a protected 19-nor-vitamin D analog having the structure

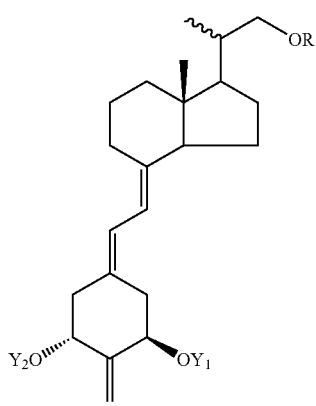

thereafter cleaving the protecting group R to form an alcohol having the structure

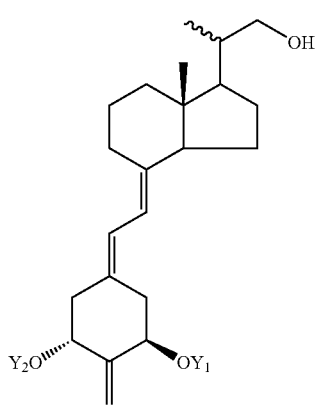

converting said alcohol to an ester having the structure

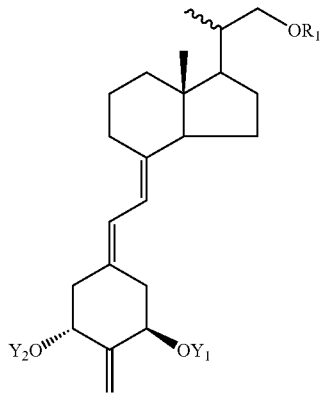

where $R_1$ is a tosyl group or a mesyl group;

reducing said ester to obtain 17β-isopropyl vitamin D derivative having the structure

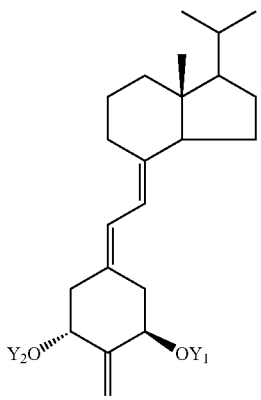

and deprotecting said 17β-isopropyl vitamin D derivative to form 1α-hydroxy-2-methylene-19-nor-homopregnacalciferol.

DISCLOSURE OF THE INVENTION

A class of 1α-hydroxylated vitamin D compounds not known heretofore are the vitamin D isomers in which the A-ring exocyclic methylene group, typical of all vitamin D system has been transposed to the carbon 2, i.e. 19-nor-vitamin D analogs, having a methylene group at the 2-position.

Structurally the novel analogs are characterized by the general formula I shown below:

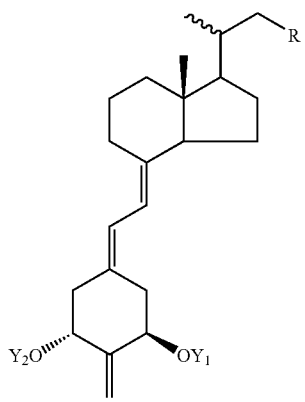

where $Y_1$ and $Y_2$, which may be the same or different, are each selected from the group consisting of hydrogen and a hydroxy-protecting group, R may be selected from the group consisting of hydrogen, hydroxyl and protected hydroxyl.

The wavy line to the methyl substituent at C-20 indicates that carbon 20 may have either the R or S configuration.

The preparation of 1α-hydroxy-20-methyl-2-methylene-19-nor-pregnacalciferol compounds (also herein referred to as 1α-hydroxy-2-methylene-19-nor-homopregnacalciferol compounds) having the basic structure I can be accomplished by a common general method, i.e. the condensation of a bicyclic Windaus-Grundmann type ketone II with the allylic phosphine oxide III:

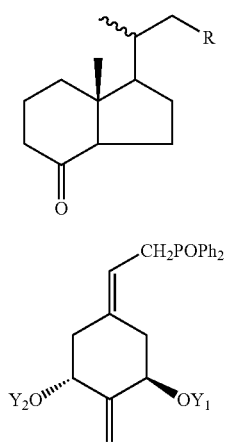

In the structures II and III, groups $Y_1$ and $Y_2$ and R represent groups defined above; $Y_1$ and $Y_2$ are preferably hydroxy-protecting groups, R is either hydrogen, hydroxyl or protected hydroxyl, it being also understood that any functionalities in R that might be sensitive, or that interfere with the condensation reaction, be suitably protected as is well known in the art. The process shown above represents an application of the convergent synthesis concept, which has been applied effectively for the preparation of vitamin D compounds [e.g. Lythgoe et al., J. Chem. Soc. Perkin Trans. I, 590 (1978); Lythgoe, Chem. Soc. Rev. 9, 449 (1983); Toh et al., J. Org. Chem. 48, 1414 (1983); Baggiolini et al., J. Org. Chem. 51, 3098 (1986); Sardina et al., J. Org. Chem. 51, 1264 (1986); J. Org. Chem. 51, 1269 (1986); DeLuca et al., U.S. Pat. No. 5,086,191; DeLuca et al., U.S. Pat. No. 5,536,713].

Hydrindanones of the general structure II are known, or can be prepared by known methods. Specific important examples of such known bicyclic ketones are Grundmann's ketone analogs (a & b) [Mincione et al., Synth. Commun. 19, 723, 1989; Peterson et al., J. Org. Chem. 51, 1948 (1986)].

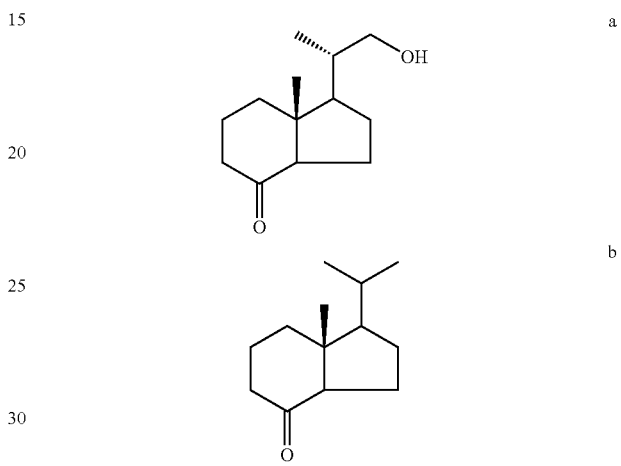

2-Methylene phosphine oxide III can be prepared according to the procedure described by Sicinski et al., J. Med. Chem, 41, 4662 (1998), DeLuca et al., U.S. Pat. No. 5,843,928.

For the preparation of the required Grundmann's ketone analog of the general structure II, a new synthetic route has been developed starting from the diol 2, easily obtained from the commercial vitamin $D_2$ as described by Sardina et al., J. Org. Chem. 51, 1264 (1986). The overall process for the synthesis of the vitamin D analog 10 is summarized by the SCHEME 1. Thus the diol 2, obtained by the ozonolysis of vitamin $D_2$, was protected as mono triethyl silyl ether 3 and the secondary hydroxyl at C-8 was oxidized with PDC to get the Grundmann's ketone 4. Wittig-Homer coupling of the conjugate base of the phosphine oxide 5, produced upon deprotonation with phenyllithium, with the protected 22-hydroxy Grundmann's ketone afforded the expected protected 19-nor-vitamin D analog 6 in a high yield. The triethylsilyl protecting group of the compound 6 was cleaved using 8:8:1 mixture of AcOH:THF:$H_2O$ to give 22-alcohol 7. This was then converted into its tosyl derivative 8 on reaction with p-toluenesulfonyl chloride in pyridine, which on reduction with $LiAlH_4$ gave the 20-methyl analog 9. The final step involved the unmasking of the silyl ethers with tetrabutylammonium fluoride to yield 1α-hydroxy-20-methyl-2-methylene-19-nor-pregnacalciferol, i.e. 1α-hydroxy-2-methylene-19-nor-homopregnacalciferol, 10. An alternative procedure for the synthesis of vitamin analog 10 involves the Wittig-Homer coupling of the Grundmann's ketone analog b with the 2-methylene phosphine oxide 5, followed by the deprotection of silyl ethers.

EXAMPLE 1

Preparation of 1α-hydroxy-2-methylene-19-nor-homopregnacalciferol (Sometimes also Referred to as 1α-hydroxy-20-methyl-2-methylene-19-nor-pregnacalcifeol) 10 a) Ozonolysis of Vitamin $D_2$

A solution of vitamin $D_2$ (2.00 g. 5.05 mmol) in absolute methanol (175 mL) and pyridine (1.75 mL) was placed in an ozonation vessel provided with a magnetic stirring bar. The solution was cooled to −78° C. while purging with oxygen. Then a stream of ozone was passed until a deep blue color appeared (1 h). The ozone flow was discontinued, and the reaction mixture was purged with oxygen (−78° C.) until no ozone remained in solution. Then $NaBH_4$ (500 mg) was added in one portion, and the resulting solution was stirred at −78° C. for 20 min while a gentle flow of $N_2$ was maintained. The reaction was allowed to stir at room temperature overnight. An additional quantity of $NaBH_4$ (500 mg) was added at room temperature, and the resulting solution was stirred for 30 min. The resulting solution was rotary evaporated to a small volume, and the residue was extracted with ether. The ethereal layers were washed with 5% HCl and $H_2O$ and then dried over $Na_2SO_4$. Filtration and concentration in vacuo afforded a residue that was flash chromatographed (75:25 mixture of hexane/ethyl acetate) to yield diol 2 (1.2 g, 82%): $^1$H NMR ($CDCl_3$) δ0.958 (3H, s, 18-$CH_3$), 1.03 (2H, d, J=6.6 Hz, 21-$CH_3$), 3.38 (1H, dd, J=10.5, 6.7 Hz, 22-H), 3.64 (1H, dd, J=10.5, 3.5 Hz, 22-H), 4.09 (1H, m, 8α-H).

b) Preparation of Silyl Ether 3

De-A,B-23,24-dinor-22-[(triethylsilyl)oxy]-cholan-8β-ol (3). To a solution of the diol 2 (100 mg, 0.472 mmol) in anhydrous acetonitrile (250 μL) and 2,6-lutidine (138 μL, 1.17 mmol) was added triethylsilyl trifluoromethanesulfonate (118 μL, 0.518 mmol). The reaction was then stirred at room temperature under argon for 2 h, then quenched with water and extracted with ethyl acetate. The organic layer was washed with brine solution, dried ($Na_2SO_4$). The organic extracts were evaporated to get the crude product, which was purified by silica gel chromatography to yield the silyl ether 3 (120 mg, 80%): $^1$H NMR ($CDCl_3$) δ 0.575 (6H, q, 3×$SiCH_2$), 0.947 (9H, t, 3×$SiCH_2CH_3$), 0.958 (3H, s, 18-$CH_3$), 1.03 (2H, d, J=6.6 Hz, 21-$CH_3$), 3.24 (1H, dd, J=9.6, 7.7 Hz, 22-H), 3.59 (1H, dd, J=3.5, 9.6 Hz, 22-H), 4.08 (1H, m, 8α-H).

c) Oxidation of the 8β-hydroxyl Group in Compound 3

De-A,B-23,24-dinor-22-[(triethylsilyl)oxy]-8-oxo-cholane (4). Pyridinium dichromate (87.6 mg, 0.232 mmol) was added to a solution of alcohol 3 (50 mg, 0.155 mmol) and pyridinium p-toluenesulfonate (10 mg) in $CH_2Cl_2$ (2 mL). The resulting orange suspension was stirred for 3 h at room temperature. Ether was added, and the resulting suspension was filtered through a short column of Celite. The filtrate was washed with a saturated aqueous solution of $CuSO_4$, and $H_2O$, dried ($Na_2SO_4$), and filtered. Removal of solvents under reduced pressure afforded the ketone, which was then purified by column chromatography. The compound was further purified by HPLC (250×10 mm Zorbax-Sil column, 4 mL/min) using 90:10 mixture of hexane/ethyl acetate as eluent. Pure protected ketone 4 (38 mg, 79%) was eluted at $R_V$ 17 mL: $^1$H NMR ($CDCl_3$) δ 0.582 (6H, q, 3×$SiCH_2$), 0.643 (3H, s, 18-$CH_3$), 0.952 (9H, t, 3×$SiCH_2CH_3$), 1.036 (3H, d, J=6.1 Hz, 21-$CH_3$), 3.29 (1H, dd, J=6.9, 9.6 Hz, one of 22-H), 3.58 (1H, dd, J=2.8, 9.6 Hz, one of 22-H).

d) Wittig-Homer Condensation of Phosphine Oxide 5 with Protected Grundmann's Ketone 4

1α-[(tert-Butyldimethylsilyl)oxy]-(20S)-20-[(triethylsilyl)oxy]methyl-2-methylene-19-nor-pregnacalciferol tert-butyldimethylsilyl ether (6). To a solution of phosphine oxide 5 (13 mg, 0.0218 mmol) in anhydrous THF (130 μL) at 0° C. was slowly added PhLi (18 μL, 0.0327 mmol) under argon with stirring. The solution turned deep orange. The mixture was cooled to −78° C. and a precooled (−78° C.) solution of protected hydroxy ketone 4 (8.5 mg, 0.0262 mmol) in anhydrous THF (170 μL) was slowly added. The mixture was stirred at −78° C. for 2 h 30 min and then at 0° C. for 18 h. Ethyl acetate was added and the organic phase was washed with brine, dried ($MgSO_4$) and evaporated. The residue was dissolved in hexane, applied on a silica Sep-Pak cartridge, and washed with hexane/ethyl acetate (99.7:0.3, 20 mL) to give 19-nor-vitamin D derivative 6. The vitamin derivative was further purified by HPLC (250×10 mm Zorbax-Sil column, 4 mL/min) using hexane/ethyl acetate (99.9:0.1) solvent system. Pure compound 6 was eluted at $R_V$ 22 mL as a colorless oil: UV (in ethanol) $\lambda_{max}$ 244, 252, 262 nm; $^1$H NMR ($CDCl_3$) δ 0.026, 0.047, 0.065 and 0.079 (each 3H, each s, 4×$SiCH_3$), 0.559 (3H, s, 18-$CH_3$), 0.593 (6H, q, 3×$SiCH_2$), 0864 and 0.894 (each 9H, each s, 2×Sit-Bu), 0.966 (9H, t, 3×$SiCH_2CH_3$), 1.019 (3H, d, J=6.5 Hz, 21-$CH_3$), 3.25 (1H, dd, J=9.5, 7.9 Hz, 22-H), 3.62 (1H, dd, J=3.4, 9.6 Hz, 22-H), 4.42 (2H, m, 1α-H, 3β-H), 4.92 and 4.96 (each 1H, each s, =$CH_2$), 5.84 (1H, d, J=11.2 Hz, 7-H) and 6.21 (1H, d, J=11.2 Hz, 6-H); MS m/z (relative intensity): 688 ($M^+$, 34), 659 ($M^+$-$CH_3$), 557 ($M^+$-$OSi(CH_3)_2$t-Bu, 50).

e) Cleavage of Triethylsilyl Ether in the Vitamin Analog 6

1α-[(tert-Butyldimethylsilyl)oxy]-(20S)-20-hydroxymethyl-2-methylene-19-nor-pregnacalciferol tert-butyldimethylsilyl ether (7). To a solution of the 19-nor-vitamin D derivative 6 (1.5 mg, 0.002 mmol) in 50 μL benzene was added 200 μL of 8:8:1 mixture of $AcOH:THF:H_2O$ and stirred for 2 h. The reaction mixture was then quenched with aqueous solution of $NaHCO_3$ and extracted with ether. The combined ether layers were washed with brine, dried ($Na_2SO_4$) and the solvent evaporated to get the alcohol which was further purified by silica column chromatography with 95:5 mixture of hexane/ethyl acetate to yield pure 7 (1 mg, 80%): $^1$H NMR ($CDCl_3$) 0.026, 0.047, 0.064 and 0.078 (each 3H, each s, 4×$SiCH_3$), 0.571 (3H, s, 18-$CH_3$), 0.864 and 0.895 (each 9H, each s, 2×Sit-Bu), 1.065 (3H, d, J=6.6 Hz, 21-$CH_3$), 3.40 (1H, dd, J=10.4, 7.0 Hz, 22-H), 3.65 (1H, dd, J=3.3, 15.4 Hz, 22-H), 4.42 (2H, m, 1α-H, 3β-H), 4.92 and 4.97 (each 1H, each s, =$CH_2$), 5.84 (1H, d, J=11.3 Hz, 7-H) and 6.21 (1H, d, J=11.3 Hz, 6-H); MS m/z (relative intensity) 574 ($M^+$, 17), 559 ($M^+$-$CH_3$, <1), 442 ($M^+$-$OSi(CH_3)_2$t-Bu, 64).

f) Conversion of the Hydroxy Compound 7 into the Tosyl Derivative 8

1α-[(tert-Butyldimethylsilyl)oxy]-(20S)-20-[(p-toluenesulfonyl)oxy]methyl-2-methylene-19-nor-pregnacalciferol tert-butyldimethylsilyl ether (8). A solution of the alcohol 7 (1 mg, 0.0017 mmol) and p-toluenesulfonyl chloride (498 μg, 0.0026 mmol) in pyridine (34 μL, 0.0043 mmol) was kept at 0° C. for 3 h. Addition of ice resulted in a suspension that was extracted with ethyl acetate/hexane. The organic extracts were washed with 5% aqueous HCl, $H_2O$, and saturated aqueous $NaHCO_3$, and dried over $Na_2SO_4$. Removal of the solvents in vacuo afforded a residue that was crystallized from hexane to yield the tosylated product 8 (1 mg, 79%).

g) Reduction of Tosyl Ester 8

1α-[(tert-Butyldimethylsilyl)oxy]-20-methyl-2-methylene-19-nor-pregnacalciferol tert-butyldimethylsilyl ether (9). To the compound 8 (1 mg, 0.0013 mmol) in anhydrous ether (2 mL) was added lithium aluminum hydride (15 μg, 0.0038 mmol). The reaction mixture was refluxed for 2 h, cooled and excess reagent was decomposed by saturated aqueous sodium chloride. The mixture was filtered and layers separated. The aqueous fraction was extracted with ether. Ether fractions were washed with water, saturated aqueous sodium chloride, dried ($Na_2SO_4$), evaporated to dryness and dried under vacuum to get the crude 17β-isopropyl vitamin D derivative 9. The compound was purified on a silica Sep-Pak cartridge using 97:3 mixture of hexane/ethyl acetate.

9: $^1$H NMR ($CDCl_3$) δ 0.025, 0.047, 0.065 and 0.078 (each 3H, each s, 4×$SiCH_3$), 0.540 (3H, s, 18-$CH_3$), 0.864 and 0.895 (each 9H, each s, 2×Sit-Bu), 0.865 (3H, d, J=6.6 Hz, 22-$CH_3$), 0.946 (3H, d, J=6.5 Hz, 21-$CH_3$), 4.42 (2H, m, 1α-H, 3βH), 4.92 and 4.97 (each 1H, each s, =$CH_2$), 5.84 (1H, d, J=11.0 Hz, 7-H) and 6.22 (1H, d, J=11.0 Hz, 6-H).

h) Deprotection of TBDMS Ethers of the Vitamin Analog 9

1α-Hydroxy-20-methyl-2-methylene-19-nor-pregnacalciferol (10). Protected vitamin 9 (750 μg, 0.0013 mmol) was dissolved in anhydrous THF (150 μL), then tetrabutylammonium fluoride (1 M solution in THF, 4 μL, 0.004 mmol) was added and the mixture was stirred at room temperature for 2 h under argon. The reaction was then quenched with water and extracted with ether, washed with brine, dried ($Na_2SO_4$), and evaporated. The residue was purified by HPLC (250×6.2 mm Zorbax-ODS reversed phase column, 2 mL/min) using methanol/water (95:5) solvent system. Pure vitamin derivative 10 was eluted at $R_V$ 9.4 mL (375 μg, 85%): UV (in ethanol) $\lambda_{max}$ 243.5, 251.5, 262.0 nm; $^1$H NMR ($CDCl_3$) δ 0.547 (3H, s, 18-$CH_3$), 0.865 (3H, d, J=6.6 Hz, 22-$CH_3$), 0.944 (3H, d, J=6.5 Hz, 21-$CH_3$), 4.48 (2H, m, 1α-H, 3β-H), 5.09 and 5.10 (each 1H, each s, =$CH_2$), 5.88 (1H, d, J=11.4 Hz, 7-H) and 6.36 (1H, d, J=11.4 Hz, 6-H); MS m/z (relative intensity) 330 ($M^+$, 100), 312 ($M^+$-$H_2O$), 287 ($M^+$-$C_3H_7$, 22).

As used in the description and in the claims, the term "hydroxy-protecting group" signifies any group commonly used for the temporary protection of hydroxy functions, such as for example, alkoxycarbonyl, acyl, alkylsilyl or alkylarylsilyl groups (hereinafter referred to simply as "silyl" groups), and alkoxyalkyl groups. Alkoxycarbonyl protecting groups are alkyl-O—CO-groupings such as methoxycarbonyl, ethoxycarbonyl, propoxycarbonyl, isopropoxycarbonyl, butoxycarbonyl, isobutoxycarbonyl, tert-butoxycarbonyl, benzyloxycarbonyl or allyloxycarbonyl. The term "acyl" signifies an alkanoyl group of 1 to 6 carbons, in all of its isomeric forms, or a carboxyalkanoyl group of 1 to 6 carbons, such as an oxalyl, malonyl, succinyl, glutaryl group, or an aromatic acyl group such as benzoyl, or a halo, nitro or alkyl substituted benzoyl group. The word "alkyl" as used in the description or the claims, denotes a straight-chain or branched alkyl radical of 1 to 10 carbons, in all its isomeric forms. Alkoxyalkyl protecting groups are groupings such as methoxymethyl, ethoxymethyl, methoxyethoxymethyl, or tetrahydrofuranyl and tetrahydropyranyl. Preferred silyl-protecting groups are trimethylsilyl, triethylsilyl, t-butyldimethylsilyl, dibutylmethylsilyl, diphenylmethylsilyl, phenyldimethylsilyl, diphenyl-t-butylsilyl and analogous alkylated silyl radicals. The term "aryl" specifies a phenyl-, or an alkyl-, nitro- or halo-substituted phenyl group.

A "protected hydroxy" group is a hydroxy group derivatised or protected by any of the above groups commonly used for the temporary or permanent protection of hydroxy functions, e.g. the silyl, alkoxyalkyl, acyl or alkoxycarbonyl groups, as previously defined. The terms "hydroxyalkyl", "deuteroalkyl" and "fluoroalkyl" refer to an alkyl radical substituted by one or more hydroxy, deuterium or fluoro groups respectively.

SCHEME I

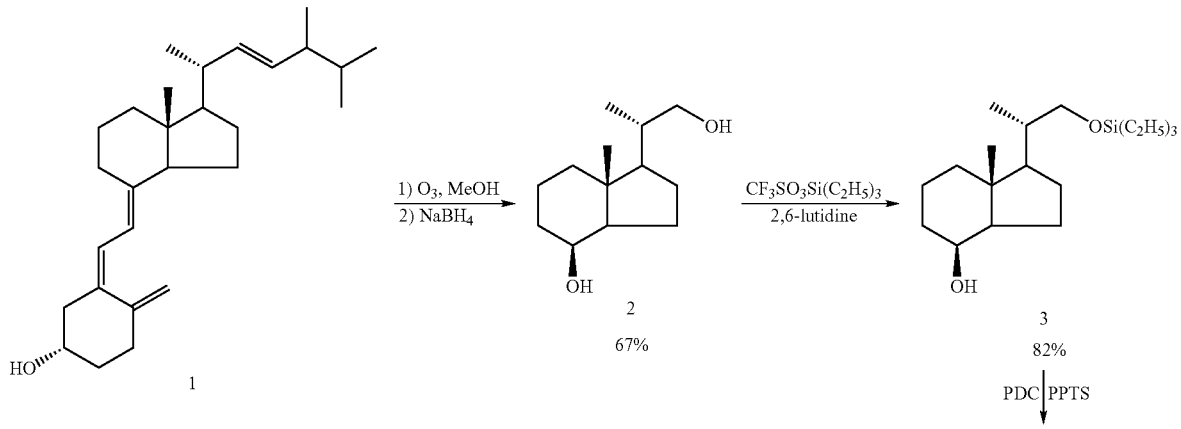

-continued
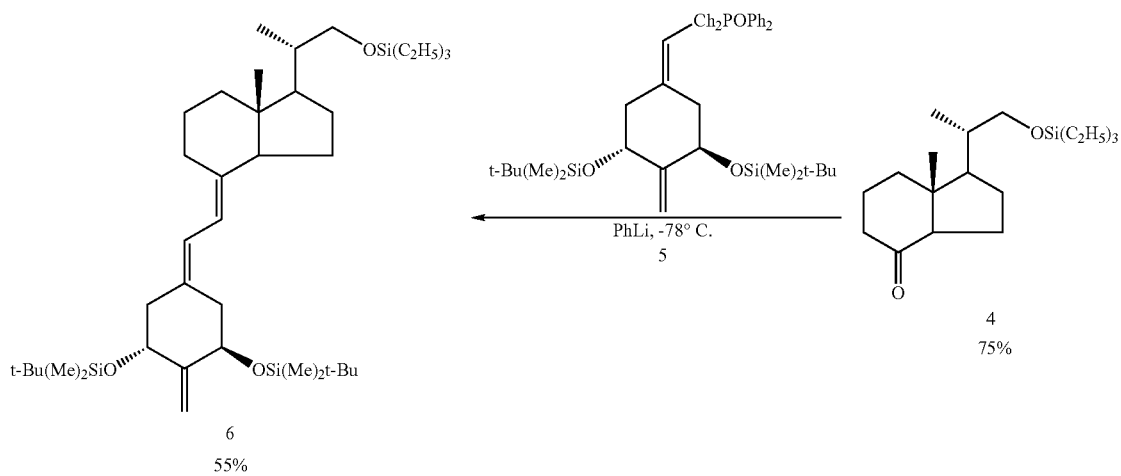
SCHEME II
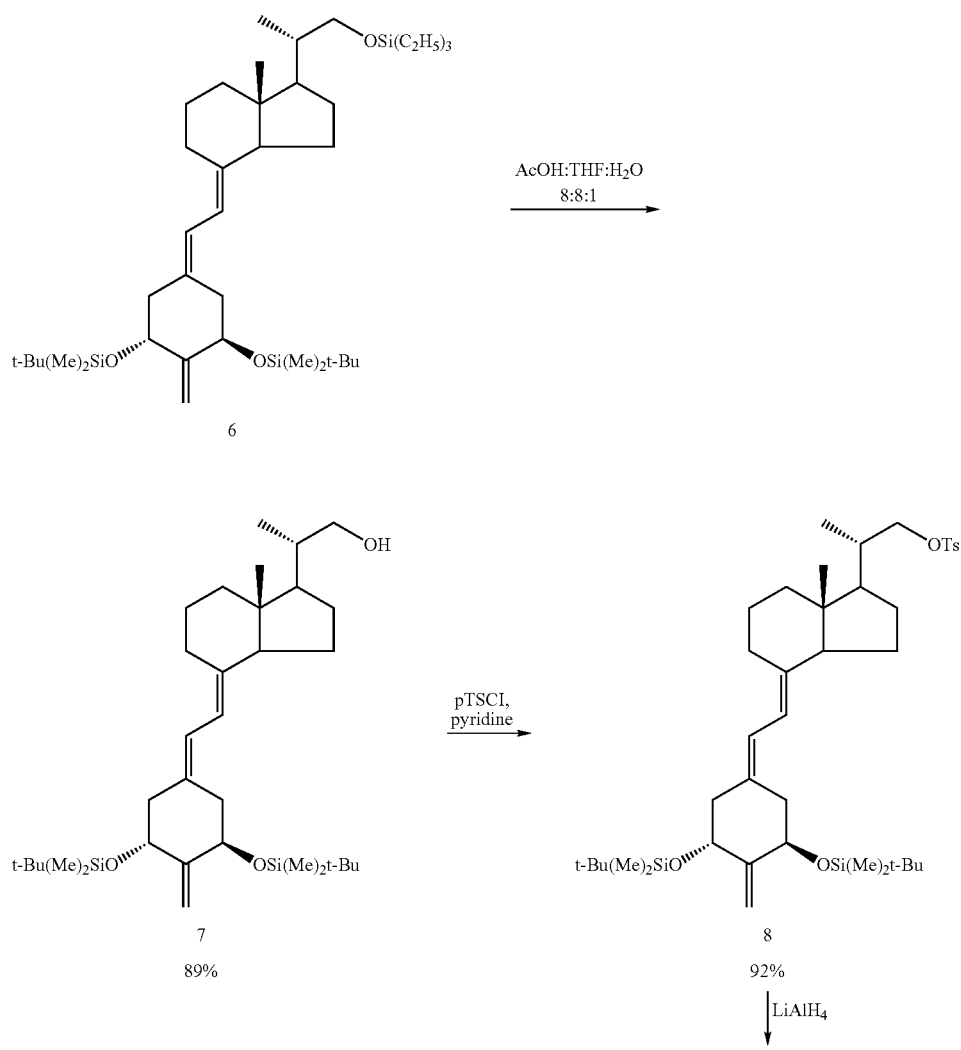

-continued

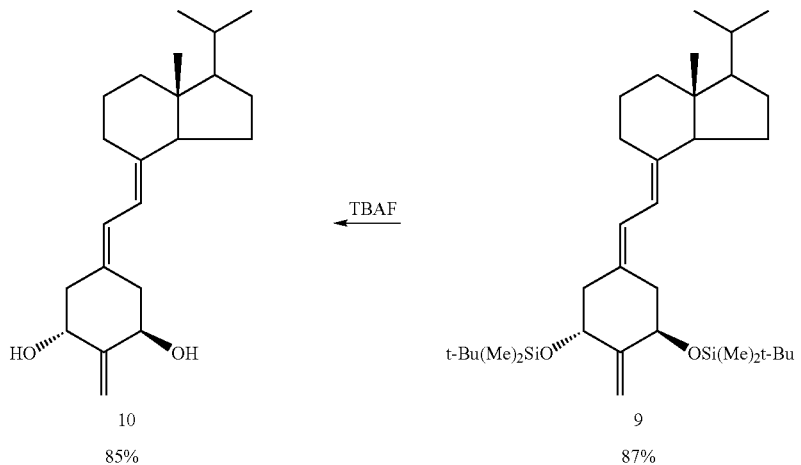

The invention claimed is:

1. A compound having the structure:

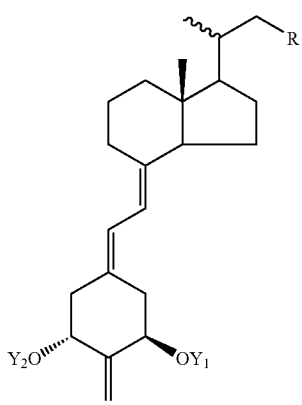

where (a) $Y_1$ and $Y_2$, which may be the same or different, are each selected from the group consisting of hydrogen and a hydroxy-protecting group, and R is selected from the group consisting of hydroxyl and protected hydroxyl; or (b) $Y_1$ and R are both hydrogen and $Y_2$ is a hydroxy-protecting group; or (c) $Y_2$ and R are both hydrogen and $Y_1$ is a hydroxy-protecting group.

2. The compound of claim 1 wherein $Y_1$ and $Y_2$ are both a t-butyl-dimethylsilyl group.

3. A compound having the structure:

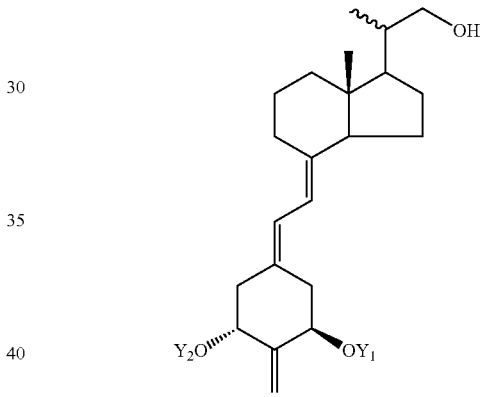

where $Y_1$ and $Y_2$, which may be the same or different, are each selected from the group consisting of hydrogen and a hydroxy-protecting group.

4. The compound of claim 3 wherein $Y_1$ and $Y_2$ are both a t-butyl-dimethylsilyl group.

5. A compound having the structure:

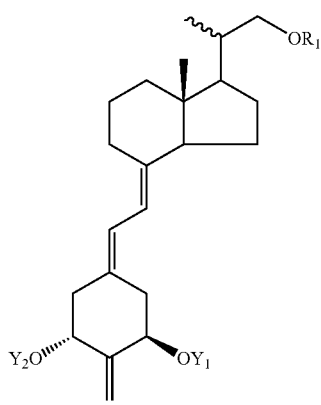

where $Y_1$ and $Y_2$, which may be the same or different, are each selected from the group consisting of hydrogen and a hydroxy-protecting group, and $R_1$ is a hydroxy-protecting group.

6. The compound of claim 5 wherein $R_1$ is a tosyl group or a mesyl group.

7. The compound of claim 5 wherein $R_1$ is a triethylsilyl group.

8. The compound of claim 5 wherein $Y_1$ and $Y_2$ are both a t-buyl-dimethylsilyl group.

9. The compound of claim 8 wherein $R_1$ is a tosyl group.

10. The compound of claim 8 wherein $R_1$ is a triethylsilyl group.

11. A compound having the structure:

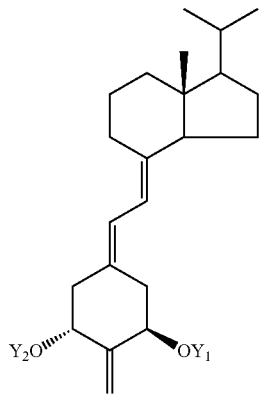

where $Y_1$ and $Y_2$, which may be the same or different, are each a hydroxy-protecting group.

12. The compound of claim 11 wherein $Y_1$ and $Y_2$ are both a t-butyl-dimethylsilyl group.

* * * * *